(12) United States Patent
Turrini et al.

(10) Patent No.: US 9,849,021 B2
(45) Date of Patent: Dec. 26, 2017

(54) ORTHOPEDIC BACK SUPPORT OR VERTEBRAL COLUMN BRACE

(75) Inventors: Alberto Turrini, Dossobuono (IT); Moreno Ferrigolo, Dossobuono (IT)

(73) Assignee: F.G.P. S.R.L., Dossobuono (IT)

( * ) Notice: Subject to any disclaimer, the term of this patent is extended or adjusted under 35 U.S.C. 154(b) by 320 days.

(21) Appl. No.: 14/401,379

(22) PCT Filed: May 15, 2012

(86) PCT No.: PCT/IB2012/052435
§ 371 (c)(1),
(2), (4) Date: Nov. 14, 2014

(87) PCT Pub. No.: WO2013/171543
PCT Pub. Date: Nov. 21, 2013

(65) Prior Publication Data
US 2015/0133843 A1  May 14, 2015

(51) Int. Cl.
*A61F 5/02* (2006.01)
*A41D 13/05* (2006.01)

(52) U.S. Cl.
CPC .......... *A61F 5/026* (2013.01); *A41D 13/0512* (2013.01); *A41D 13/0531* (2013.01)

(58) Field of Classification Search
CPC ...... A61F 5/00; A61F 5/01; A61F 5/02; A61F 5/026; A61F 5/028; A41D 13/0512;
(Continued)

(56) References Cited

U.S. PATENT DOCUMENTS 385,429 A * 7/1888 Sohner ............... A45F 5/00
                                                   224/201
3,282,264 A   11/1966 Connelly
(Continued)

FOREIGN PATENT DOCUMENTS

DE    102009050385 A1   5/2011
WO    2007043079 A1   4/2007

OTHER PUBLICATIONS

International Search Authority, Search Report for International Application PCT/IB2012/052435, dated Jan. 23, 2013 (EPO), 2 pages, The Hague, Netherlands.

*Primary Examiner* — Keri J Nelson
(74) *Attorney, Agent, or Firm* — Ference & Associates LLC

(57) ABSTRACT

A brace (10) which can be used in the orthopedic sector for correctly blocking and anatomically supporting the vertebral column, substantially consisting of a semirigid slat (11), with elongated vertical development, shaped in accordance with the vertebral column and thus making it possible to follow and support the column, the lower part being attached to straps (12) which are fixed at the front to an abdominal plate (13), wrapping around the waist, and the upper part to the end of straps (14) which also couple to the same abdominal plate (13), passing through loops (15) positioned at the sides, there being, in the initial part of the straps (14), that is to say in the coupling area (16) of the casing that encloses the semirigid slat and to a certain extent the section towards the front of the brace, a pocket (17) surrounded by stitching and in which there is a slit (18), said pocket being designed to accommodate a stiffening element (19) with a substantially arched shape.

4 Claims, 3 Drawing Sheets

(58) Field of Classification Search
CPC ......... A41D 13/0531; A45F 3/00; A45F 3/04; A45F 2003/006; A45F 2003/008; A45F 2003/045; A45F 3/047
USPC ............ 602/19; 2/467, 44, 45; 224/257–266
See application file for complete search history.

(56) References Cited

U.S. PATENT DOCUMENTS

| | | |
|---|---|---|
| 5,362,304 A | 11/1994 | Varn |
| 2004/0133138 A1 | 7/2004 | Modglin |
| 2010/0262054 A1* | 10/2010 | Summit ................. G06F 17/50 602/14 |

* cited by examiner

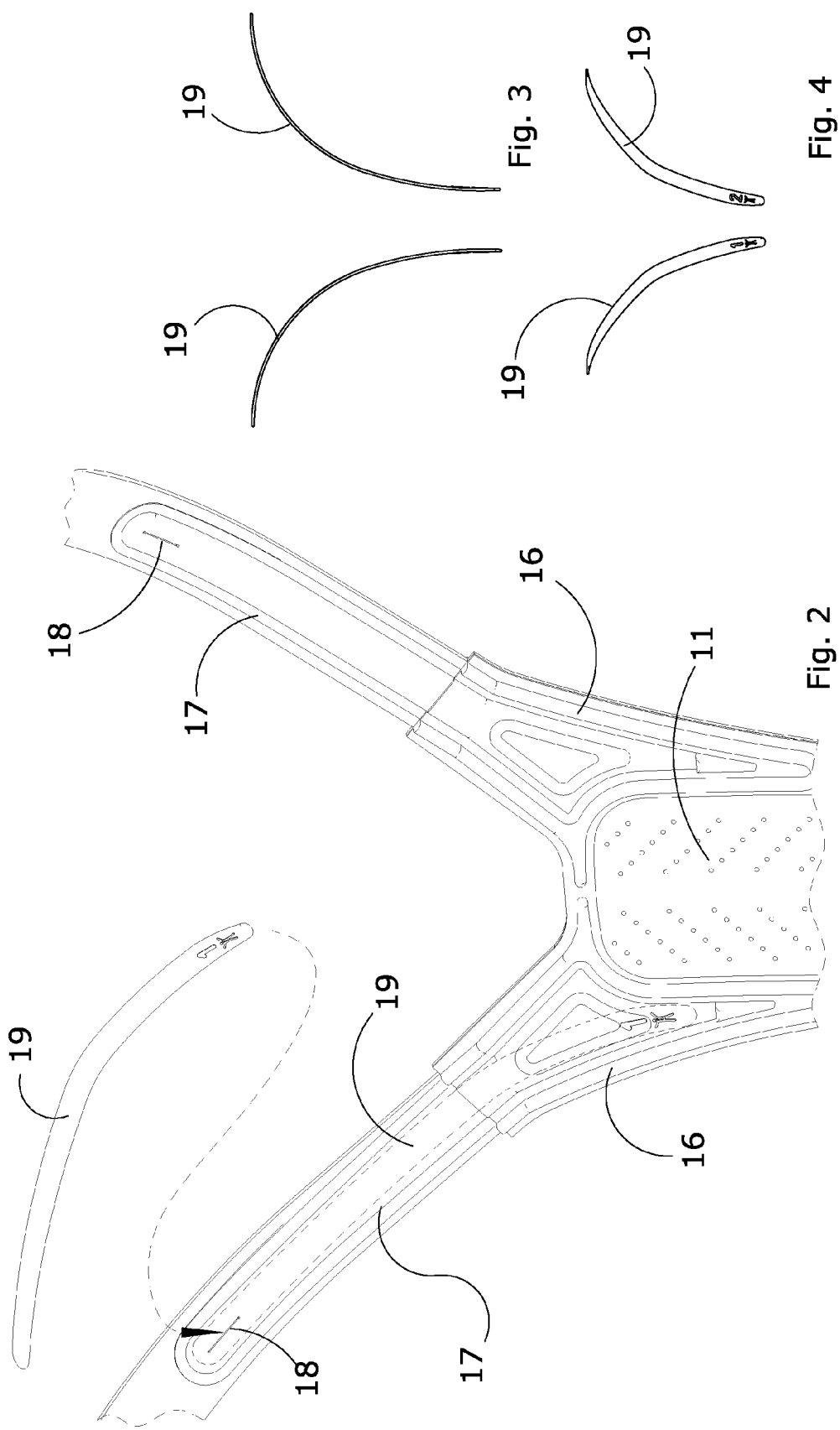

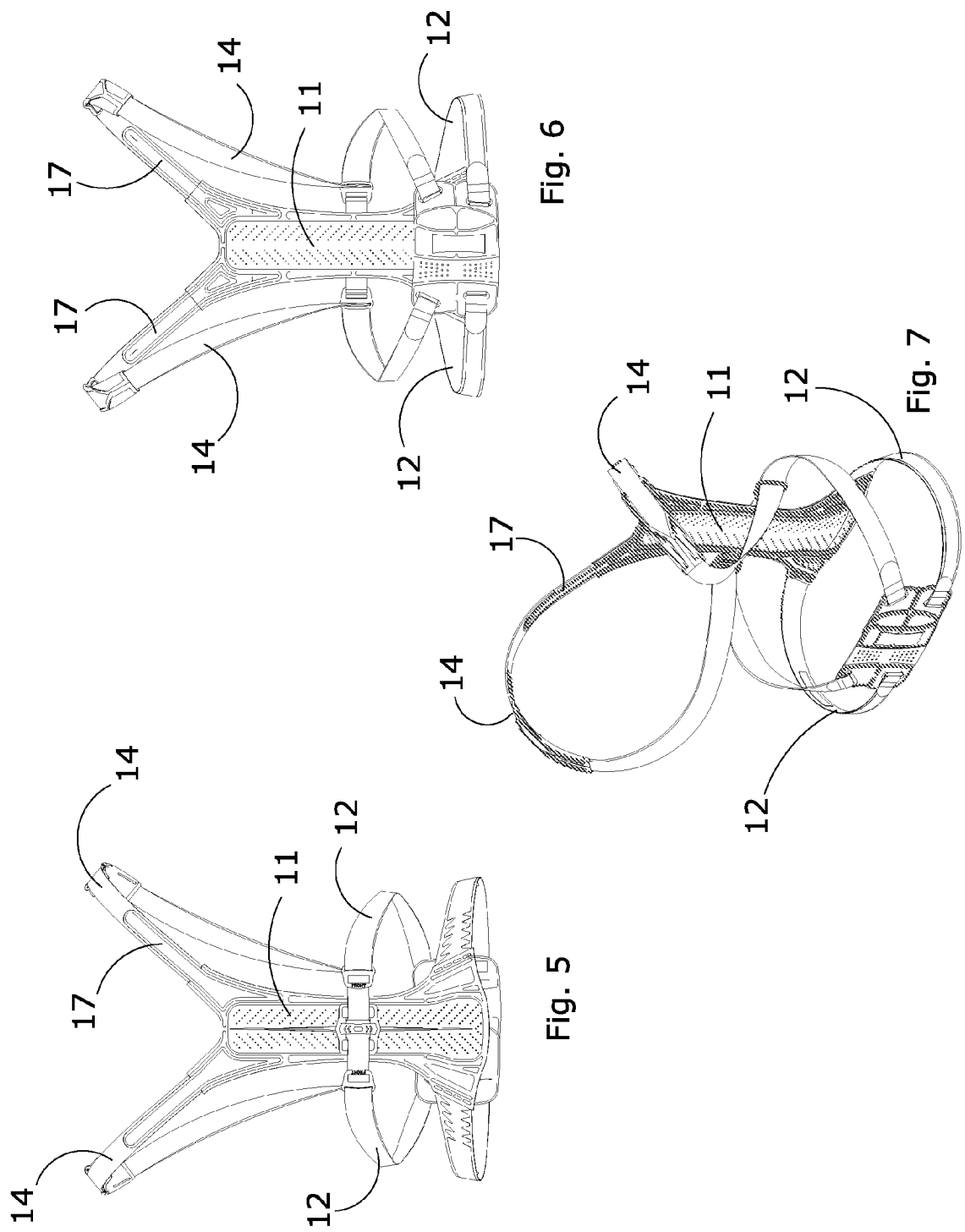

ORTHOPEDIC BACK SUPPORT OR VERTEBRAL COLUMN BRACE

TECHNICAL FIELD

This invention concerns an orthopedic back support or brace for the vertebral column, which can be used to support the spine of subjects with articular problems of the back or suffering from osteoporosis.

More specifically, this invention refers to an orthopedic back support which, with respect to known solutions, presents the advantage of comprising shoulder straps that contain a core made from preformed plastic material designed to keep the shoulder straps "in shape" when the brace is not being worn.

This solution is particularly advantageous for the user of the brace, especially in the case of elderly patients or those with motor difficulties, since it makes the brace easier to put on.

This invention can be applied in the medical and orthopedic industry and particularly in the production sector of orthopedic jackets in general but also of prostheses and braces mainly used in conservative, post-traumatic, rehabilitation and post-operative therapy.

BACKGROUND ART

It is known that with some diseases or some orthopedic type disorders of the spinal column or the trunk in persons subject for example to osteoporosis or other degenerative inflammatory disorders, or following injury, it is necessary to wear particular jacket-type or back braces or orthoses which guarantee a certain degree of support for the patient, absorbing the most intense stresses that the trunk is submitted to.

Particularly useful in all types of backache in less acute phases of osteoporosis, by activating the muscles in the back, the brace favours straightening of the trunk, reducing the kyphosis caused by osteoporosis.

Various types of jackets, braces or orthoses designed to support and contain the trunk are currently known and available. These are generally structures which rest against the spinal column and which mainly consist of a plate which stiffens the vertebral column, and thus has the same shape, and which is attached to the trunk and held in place by means of straps.

These devices consist, in fact, of a rigid vertically elongated frame, made from metal and shaped to adhere to the vertebral column, the frame being fixed to the user's trunk by fastening means which are usually the strap or jacket type.

If strap fastening means are used, these consist of harnesses with ends attached to the rigid frame and which wrap around the trunk and are secured in place by appropriate adjustable type means of restraint.

These straps are connected to the central body of the brace positioned in correspondence with the vertebral column and are in contact with various anatomical parts of the body.

In particular, it is possible to distinguish between two types of straps that are attached to a back brace and which allow it to be fixed to the trunk:

- a first upper strap, which starts from the upper end of the back brace and which, passing below the shoulder-humerus joint, has an elastic element which is positioned more or less at the mid point of the brace and which terminates on the front support plate that must be positioned in the patient's abdominal area;
- a second strap which starts from the lower part of the back brace, passing over the patient's sides, and terminates on the aforesaid plate.

This system of straps must be adjusted in length in order to guarantee the correct adherence of the brace to the patient's vertebral column and the correct thrust system that acts on the anatomical parts involved.

The technical problem encountered with these solutions concerns, in this specific case, the difficulty involved in putting the brace on when it must be worn by an elderly patient or with difficulties in moving the limbs.

Traditional braces are in fact made in such a way that when they are not being used, even if correctly folded away, the back frame and all the relative straps become somewhat disordered, and when the brace is picked up again it is like a harness with limp straps, making it difficult to understand which loop the arms should be put through so that the straps wrap over the shoulders at the top and around the waist at the bottom.

The problem described above is even more evident if the brace has to be put on by a person with movement difficulties, who, without another person to help, often prefers to give up due to the practical difficulties encountered in trying to put the brace on.

DESCRIPTION OF THE INVENTION

This invention proposes to provide a dorsal orthopedic support or brace for the vertebral column, which can eliminate or at least reduce the problems described above.

In particular, the dorsal orthopedic support or brace for the spinal column according to the invention resolves the problems encountered in putting the brace on by the use of means consisting of a core in preformed plastic material which is designed to keep the shoulder straps "in shape" when the brace is not being worn. This solution can be particularly useful as it makes the brace easier to put on.

This is achieved by means of a dorsal orthopedic support or brace for the spinal column according to the invention with the features described in the main claim.

The dependent claims describe advantageous embodiments of the invention.

The proposed aims are achieved, according to the invention, by a dorsal orthopedic support or brace for the spinal column, whose particularity is being able to insert, in relative pockets on the shoulder straps, flexible stiffening elements made from preformed plastic material that keep the straps in shape in order to allow the user to put the brace on very easily and without the help of anyone else.

DESCRIPTION OF THE DRAWINGS

Other features and advantages of the invention will become evident on reading the following description of one embodiment of the invention, provided as a non-binding example, with the help of the accompanying drawings in which:

FIG. 2 represents a detail of the brace showing the two pockets present on the respective shoulder traps, in which the flexible stiffening elements are inserted;

FIG. 3 shows a schematic view of the two flexible stiffening elements seen in profile and facing each other;

FIG. 4 shows a schematic view of the two flexible stiffening elements seen in prospective view;

FIGS. 5 to 7 show schematic views of braces seen from behind, from the front and in a prospective front view.

DESCRIPTION OF ONE EMBODIMENT OF THE INVENTION

Figure 1:
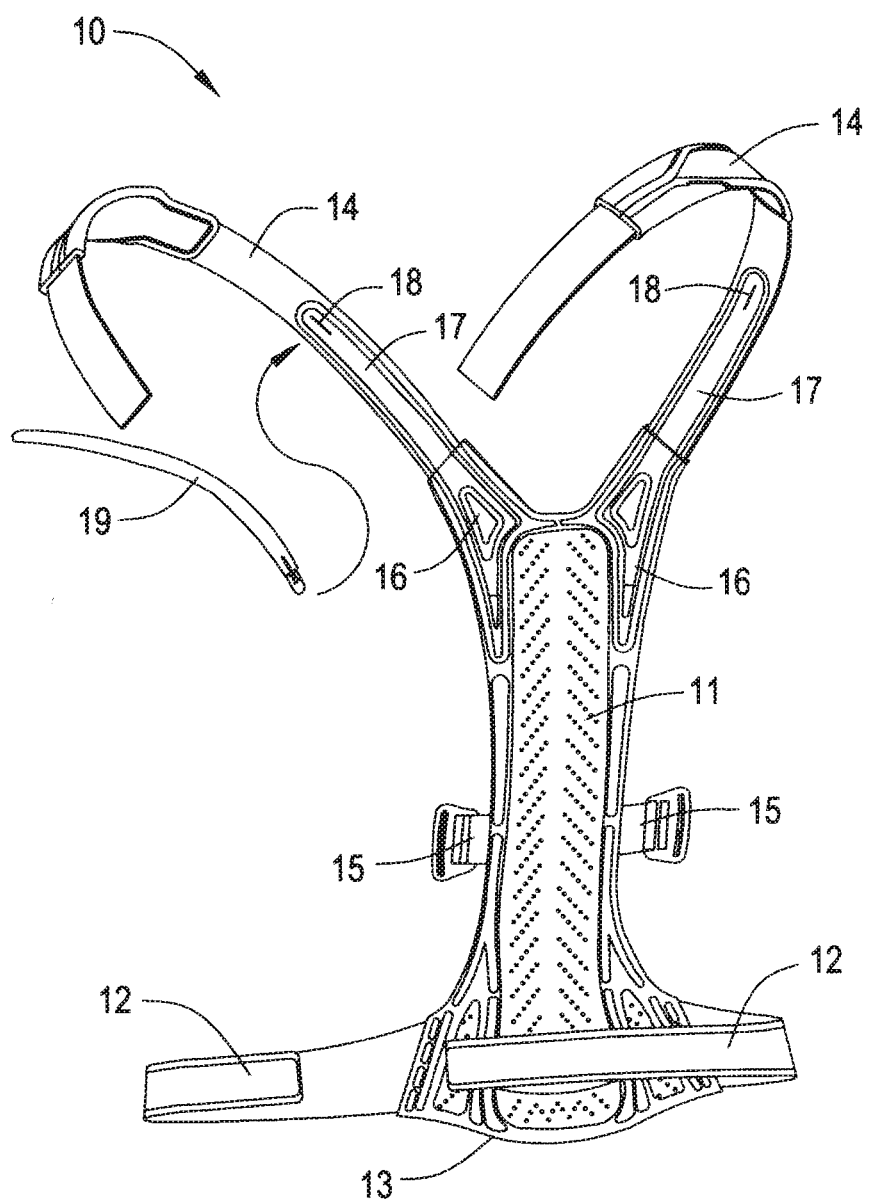
FIG. 1 is a schematic view of a brace with shoulder strap reinforcements inserted in the relative pockets according to the invention.

The brace according to the invention, mainly used in the orthopedic sector for blocking and anatomically supporting the vertebral column, indicated overall with the reference number 10, therefore foresees the use of means that make it possible to overcome the problems caused by the difficulties encountered when putting the brace on.

More specifically, the brace 10 consists of a semirigid slat 11, with elongated vertical development, shaped in accordance with the vertebral column and thus making it possible to follow and support the column, the lower part being attached to straps 12 which are fixed at the front to an abdominal plate 13, wrapping around the waist, and the upper part to the end of straps 14 which also couple to the same abdominal plate 13, passing through loops 15 positioned at the sides of the body.

According to the invention, the initial part of the straps 14, that is to say the coupling zone 16 of the casing that encloses the semirigid slat and to a certain extent the section towards the front of the brace, is provided with a pocket 17 surrounded by stitching.

The pocket 17 is provided with a slit 18 designed to accommodate a stiffening element 19 with a substantially arched shape.

The stiffening element consists of a core made from preformed plastic material designed to keep the shoulder straps "in shape" when the brace is not being worn.

This solution can be particularly useful for the person wearing the brace especially if the person has difficulty in moving the limbs as it makes the brace easier to put on.

The stiffening elements 17, which are made from plastic or other material suitable for the purpose, are positioned in such a way that they can be removed, if necessary, through the slit 18 in the shoulder strap.

In this specific case there are at least two pockets and stiffening elements, that is to say one for each shoulder strap 14, but the other straps can also be equipped with them, according to requirements.

The stiffening elements 17 are made according to anatomical curvatures specifically adapted to follow the curvature of the upper body, and can also have varying thicknesses, for example they can be thicker in the lower part and become thinner in the upper part in order to differentiate the flexion zones.

The use of the brace is therefore evident, since the easiness of putting the brace on is due to the fact that the stiffening elements keep the straps in shape, making the brace easy and quick to put on.

The invention is described above with reference to a preferred embodiment. It is nevertheless clear that the invention is susceptible to numerous variations that lie within its scope, in the framework of technical equivalents.

The invention claimed is:

1. An orthopedic brace for correctly blocking and anatomically supporting a vertebral column, comprising a semirigid slat enclosed in a casing and having an elongated vertical development, shaped in accordance with the vertebral column and thus making it possible to follow and support the column, a lower part of the slat being attached to a respective pair of waist straps which are fixed at a front to an abdominal plate, and an upper part of the slat being attached to a respective pair of shoulder straps which are also fixed to the abdominal plate, passing through loops positioned at a side of the slat, wherein at least a portion of each of the pair of shoulder straps comprises a pocket, each pocket accommodating a removable stiffening element that is introduced into the pocket through a corresponding slit, the stiffening element having an arcuated shape keeping the shoulder strap in shape thereby enhancing the wearability of the orthopedic brace by a patient.

2. The orthopedic brace according to claim 1, wherein each stiffening element consists of a core, made from preformed plastic.

3. The orthopedic brace according to claim 1, wherein the stiffening elements are made according to anatomical curvatures specifically shaped to follow the curvature of an upper body.

4. The orthopedic brace according to claim 1, wherein the stiffening elements comprise varying thicknesses, wherein the stiffening elements are thicker in the lower part and become thinner in the upper part in order to differentiate the flexion zones.

* * * * *